US012758224B2

(12) United States Patent
Kelley et al.

(10) Patent No.: US 12,758,224 B2
(45) Date of Patent: Oct. 13, 2026

(54) DEVICE AND METHOD TO PREVENT LEAKAGE

(71) Applicant: SAFEGUARD SURGICAL, INC., Tampa, FL (US)

(72) Inventors: Scott T. Kelley, Tampa, FL (US); Jill Kelley, Tampa, FL (US)

(73) Assignee: SAFEGUARD SURGICAL, INC., Tampa, FL (US)

( * ) Notice: Subject to any disclaimer, the term of this patent is extended or adjusted under 35 U.S.C. 154(b) by 165 days.

(21) Appl. No.: 18/241,287

(22) Filed: Sep. 1, 2023

(65) Prior Publication Data

US 2024/0074758 A1 Mar. 7, 2024

Related U.S. Application Data

(60) Provisional application No. 63/523,129, filed on Jun. 26, 2023, provisional application No. 63/452,194, filed on Mar. 15, 2023, provisional application No. 63/452,193, filed on Mar. 15, 2023, provisional application No. 63/452,197, filed on Mar. 15, 2023, provisional application No. 63/404,202, filed on Sep. 7, 2022.

(51) Int. Cl.

*A61B 17/11* (2006.01)
*A61B 17/00* (2006.01)
*A61B 17/12* (2006.01)
*A61L 27/36* (2006.01)

(52) U.S. Cl.

CPC ....... *A61B 17/1114* (2013.01); *A61L 27/3629* (2013.01); *A61B 2017/00893* (2013.01); *A61B 2017/00951* (2013.01); *A61B 2017/1107* (2013.01); *A61B 2017/1132* (2013.01); *A61B 2017/12004* (2013.01)

(58) Field of Classification Search

CPC ...... A61B 17/1114; A61B 2017/00004; A61B 2017/00557; A61B 2017/00893; A61B 2017/00951; A61B 2017/1107; A61B 2017/1132; A61B 2017/12004; A61L 27/3629

See application file for complete search history.

(56) References Cited

U.S. PATENT DOCUMENTS 5,720,755 A * 2/1998 Dakov .................. A61B 17/11 606/139
6,620,178 B1 9/2003 Brotz
(Continued)

OTHER PUBLICATIONS

Final Office Action on U.S. Appl. No. 18/505,378 dated Apr. 28, 2025.
(Continued)

*Primary Examiner* — Mohamed G Gabr
*Assistant Examiner* — Khoa Tan Le
(74) *Attorney, Agent, or Firm* — Foley & Lardner LLP

(57) ABSTRACT

Method and device to prevent leakage of an intestine during surgery. The device is a tubular straw like device formed as one piece and having a first end opening, a second end opening and a lumen extending through an entire length of the device. The device can include an enlarged diameter rim to provide a radial force against the intestine. The device is placed at an anastomotic site of two intestine portions and attached by adhesive. The device can be used to close off perforations of body lumens.

20 Claims, 3 Drawing Sheets

(56) References Cited

U.S. PATENT DOCUMENTS

| | | | | |
|---|---|---|---|---|
| 8,092,472 | B2 | 1/2012 | Cerier | |
| 8,663,086 | B2 | 3/2014 | Duncan et al. | |
| 9,649,185 | B2 | 5/2017 | Bangera et al. | |
| 9,827,135 | B2 | 11/2017 | Fong et al. | |
| 10,667,816 | B2 | 6/2020 | Agarwal et al. | |
| 11,896,229 | B2 | 2/2024 | Pic et al. | |
| 2001/0039425 | A1 | 11/2001 | Dakov | |
| 2003/0113359 | A1 * | 6/2003 | Iyer et al. | A61P 9/00 514/56 |
| 2004/0054405 | A1 * | 3/2004 | Richard | A61B 17/11 623/1.36 |
| 2007/0100420 | A1 | 5/2007 | Kavanagh et al. | |
| 2008/0255650 | A1 * | 10/2008 | Kelley | A61B 17/1114 623/1.42 |
| 2009/0281634 | A1 | 11/2009 | Abell et al. | |
| 2010/0010517 | A1 | 1/2010 | Stopek et al. | |
| 2010/0010518 | A1 * | 1/2010 | Stopek | A61B 17/11 606/153 |
| 2011/0098732 | A1 | 4/2011 | Jacobs | |
| 2011/0137428 | A1 | 6/2011 | Terliuc | |
| 2011/0319902 | A1 | 12/2011 | Epstein | |
| 2017/0151049 | A1 * | 6/2017 | La Francesca | A61F 2/82 |
| 2018/0078257 | A1 | 3/2018 | Buttar et al. | |
| 2018/0353653 | A1 | 12/2018 | Reid et al. | |
| 2021/0113323 | A1 | 4/2021 | Hedberg | |
| 2021/0236131 | A1 | 8/2021 | Anderson et al. | |

OTHER PUBLICATIONS

Non-Final Office Action on U.S. Appl. No. 18/505,378 dated Feb. 10, 2025.

Non-Final Office Action on U.S. Appl. No. 18/505,378 dated Jul. 30, 2024.

Non-Final Office Action on U.S. Appl. No. 18/505,378 dated Aug. 11, 2025.

Notice of Allowance on U.S. Appl. No. 18/505,378 dated Mar. 17, 2026.

* cited by examiner

DEVICE AND METHOD TO PREVENT LEAKAGE

CROSS REFERENCE OF RELATED APPLICATIONS

This application claims priority from provisional patent application Ser. No. 63/452,193 filed Mar. 15, 2023, provisional patent application Ser. No. 63/404,202 filed Sep. 7, 2022, provisional patent application Ser. No. 63/452,194, filed Mar. 15, 2023, provisional patent application Ser. No. 63/452,197 filed Mar. 15, 2023, and provisional application Ser. No. 63/523,129 filed on Jun. 26, 2023. The entire contents of each of these applications are incorporated by reference.

FIELD OF THE INVENTION

This application is directed to a device for insertion into body lumens to provide protection from leakage during and/or after surgical procedures and/or seal a perforation and methods of using the device.

BACKGROUND

The gastrointestinal (GI) tract extends from the esophagus to the anus and serves many functions, including nutrition, hydration, and disease prevention. Resection of a portion of the GI tract, such as esophagus, stomach, small intestine, large intestine or colon, is performed on a patient under general anesthesia. An incision is typically made in the abdomen, chest or neck and a diseased portion is removed. The healthy ends that remain are sewn or stapled together and the incision is closed through the procedure known as anastomosis. There is substantial risk of the patient leaking at the site of the anastomosis even if the surgeon follows best practices. Leakage may lead to contamination of the peritoneal or thoracic cavity, sepsis and even death. Leakage may be evident immediately or it may be delayed at the site of anastomosis, regardless of the skill of the surgeon.

Although research to decrease failure rates of resection/anastomosis has been considerable, success has been elusive. Advances in minimally invasive procedures allow surgeons to perform resection and anastomosis using laparoscopic or thoracoscopic technologies. However, many surgeons are unwilling to use less invasive procedures due to the inherent risks of leakage and severity of the complications of leakage from the GI tract. As an alternative to connecting the two intestinal ends or to protect the newly created anastomosis, the surgeon may perform an ostomy or stoma, exteriorizing a portion of the intestine and leaving a patient with an opening on the abdomen or neck. Such procedures, however, involve having the patient wear an external pouch to collect intestinal waste. Possible infection and restrictions on patient lifestyles make this option unattractive. If an anastomosed site leaks, then a surgeon often opts to perform an ostomy to prevent any further sepsis, morbidity or death of the patient.

It would be advantageous to provide a device to reduce risks of leakage at the anastomotic site.

In some procedures, the surgeon utilizes a temporary colostomy bag to protect the anastomotic site from contact with the stool post-surgery. It would be advantageous to provide a device to protect the area to avoid the need for such colostomy bags.

It would also be advantageous to provide a device to close off perforations in intestines or body lumens.

SUMMARY OF THE INVENTION

In one aspect, the present disclosure provides a device in the form of a biodegradable tubular structure to provide support and stability for anastomosis of a lumen and/or reduce leakage at the anastomotic site. An adhesive can be utilized to attach the tubular structure to the body lumens and the adhesive can also provide a sealant. The device can be placed to prevent leaks, i.e., to prophylactically prevent leaks at the time of surgery rather than placed after a leak occurs. The tubular device of the present invention is in the form of a straw with a thin wall and a lumen extending therethrough, and has an open proximal and distal end to enable flow therethrough. The tubular device in some embodiments has a ribbed rim or can be a colon-shaped device. ("Top" referring to the portion/region closer to the head of the patient).

In another aspect of the present disclosure, the biodegradable tubular device can be used to close off perforations, tears, rips or ulcers of body lumens, such as the intestine, which need to be repaired or protected.

In another aspect of the present disclosure, the biodegradable tubular device can be used to close off leaks of the intestine or other body lumens if it develops after surgery.

In another aspect of the present disclosure, the tubular device can be made of tissue engineered material, e.g., from tissue generated organs, and placed in the colon to provide extra support to seal and prevent leakage.

In accordance with another aspect of the present disclosure, a method to prevent leakage in an intestine is provided comprising the steps of a) positioning a tubular straw like device in a lumen of the first intestine to be attached to the second intestine at an anastomotic site; and b) securing the device to the intestine utilizing an adhesive. The device can include a treatment or healing substance adhered thereto.

In accordance with another aspect of the present disclosure, a method to seal a perforation in a body lumen is provided comprising a) positioning a tubular straw like device in the body lumen, the device having a rim having an enlarged diameter to provide a radial force against the intestine; and b) securing the device to a wall of the body lumen utilizing an adhesive, the rim preventing backflow past the rim.

The methods utilize in some embodiments a tubular device having an enlarged rim providing a diameter larger than other regions of the device. The rim is at the top portion of the device and in some embodiments provides a radial force against the tissue, e.g., colon wall, to help secure the device in place. The device can be held in place by an adhesive. In preferred embodiments, the adhesive utilized has a dual function: adhering the device to the tissue, e.g., luminal wall, and providing a seal to prevent unwanted flow.

In accordance with another aspect of the present disclosure a device to limit leakage of a lumen is provided, the device comprising a tubular straw like body and having a rim, the device composed of a tissue engineered material and held in place at the rim by an adhesive.

In accordance with another aspect of the present disclosure, a device to limit leakage of a luminal region of a body of a patient is provided, the device comprising a tubular straw like configuration having an outer wall and an inner wall defining a lumen extending through the device, the device attachable to the region via adhesive.

BRIEF DESCRIPTION OF THE DRAWING

So that those having ordinary skill in the art to which the subject invention appertains will more readily understand how to make and use the apparatus (device) disclosed herein, preferred embodiments thereof will be described in detail hereinbelow with reference to the drawings, wherein:

FIGS. 5 and 6 are perspective views of an alternate embodiment of the device of the present disclosure placed over the first and second intestine portions, wherein;

FIG. 5 shows the tubular device inserted over the first intestine portion, the second intestine portion not yet attached; and FIG. 6 shows the tubular device positioned over the first and second intestine portions and the second intestine portion placed in apposition (abutment) with the first intestine portion;

DETAILED DESCRIPTION OF THE DRAWINGS

According to aspects of the present disclosure, devices disclosed are in the form of a covered stent providing a scaffold inserted between or into the lumen ends to be anastomosed to provide stability and/or structure to the anastomosed lumen.

The device provides a tubular structure, also referred to herein as a straw-like structure.

The tubular straw-like structure is impermeable and preferably composed of a biodegradable material which will degrade within the body after a period of time. The tubular structure in some embodiments provides structure and/or stability to the body lumens and/or protection from leakage. The tubular structure has a thin wall and a lumen extending therethrough, and has an open top and bottom end. "Top" and "bottom" as used herein refer to orientation wherein top is closer to the patient's head and bottom is further from the patient's head. Also, top and bottom as used herein relates to direction of flow of body fluids or substances, e.g., the stool passes from the top to bottom. Proximal as used herein can also refer to the top portion and distal refer to the bottom portion, also relating to flow/passage.

The tubular structure can be formed of one piece which provides the advantages of ease of manufacture and more flexibility as opposed to the use of covered stents which need to have an impermeable cover attached to the inner structure, e.g., frame.

In some embodiments, the tubular device is used with anastomosis of two body lumens, such as two portions of the intestine. In other embodiments, the tubular device is used in an area to be radiated to limit tissue damage. In still other embodiments, the tubular device can used in cases of perforation, such as a perforation of the intestine secondary to diverticulitis or iatrogenic perforation, to seal the perforation. Various other clinical applications of the tubular straw-like structure are also contemplated.

Figure 1:
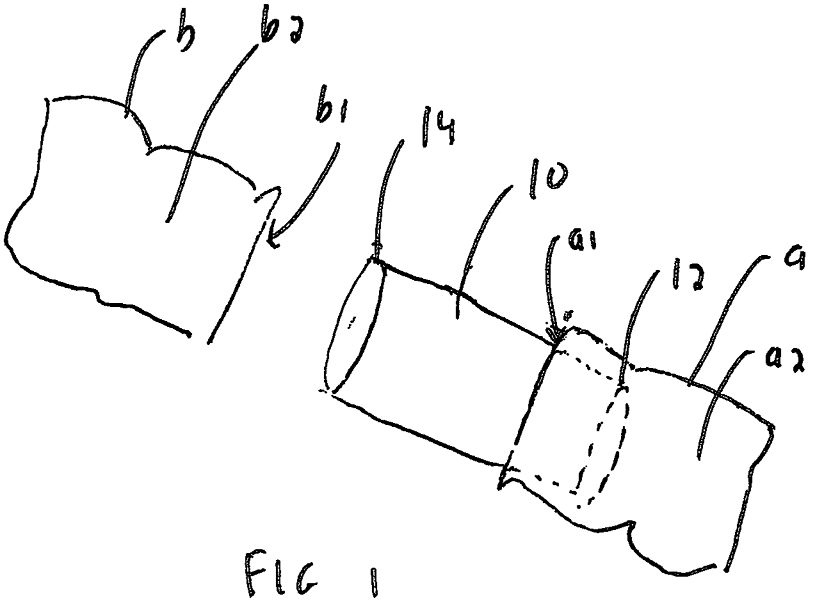
FIG. 1 is a perspective view of an embodiment of the tubular device of the present disclosure shown inserted into a lumen of a first intestine portion (section), the second intestine portion (section) not yet attached.
Figure 2:
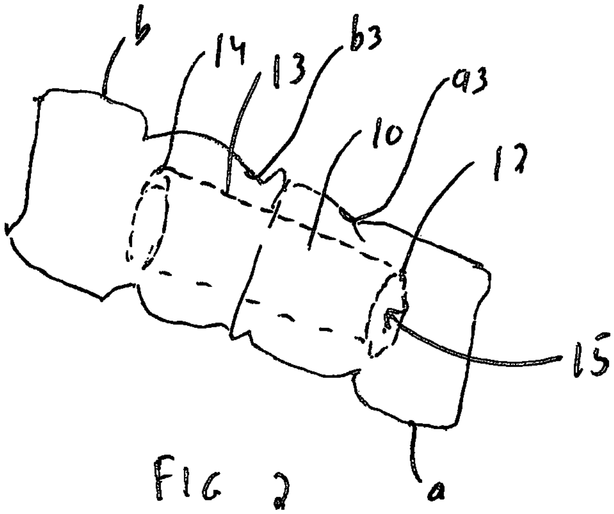
FIG. 2 is a perspective view similar to FIG. 1 showing the tubular device inserted into the lumen of the second intestine portion and second intestine portion placed in apposition (abutment) with the first intestine portion.

Referring now to the drawings and particular embodiments of the present disclosure, wherein like reference numerals identify similar structural features of the devices throughout the several views, the device (stent) of a first embodiment is designated generally by reference numeral 10. Device 10 is in the form of a biodegradable straw and has a first open end 12 and a second opposite open end 14. The device can have the dimensions set forth above. First end 12 is dimensioned, i.e., outer dimension, to be inserted into opening a1 and into lumen a2 of first intestine portion a and second end 14 is dimensioned, i.e., outer dimension, to be inserted into opening b1 and into lumen b2 of second intestine portion b. Thus, the inner diameter (ID) of the lumen is greater than the outer diameter (OD) of device 10. FIG. 1 illustrates first end 12 of device 10 inserted into lumen portion a and not yet inserted into lumen portion b; FIG. 2 illustrates device 10 inserted into both intestine portions a, b and the portions a, b are in contact (i.e. abutment) for anastomosis. The inner diameter (inner lumen 15) of device 10 is dimensioned to accommodate body fluid flow and maintain unobstructed passage through the intestine. Note the drawings of FIGS. 1-9 show a large space between the intestine wall and device for clarity while in application, the device OD would be close to the lumen ID as explained below.

In use, a lumen, such as a colon, is separated and a diseased portion is removed. After removal, the surgeon inserts one end of the tubular device 10 into one end of the separated lumen or the separated lumen end is placed over the device 10. The second end of the tubular device 10 is then inserted into the other lumen or the lumen end is placed over the device 10, and the two lumens are attached to each other by various methods such as suturing, stapling and/or use of an adhesive to create an anastomotic site.

The tubular device 10 inserted prior to anastomosis acts as a prophylactic measure against leakage and/or soilage and prevents the inconvenience and frequent complications associated with treating leaking anastomosed lumens. Additionally, the use of the device may prevent scarring and may eliminate or reduce constrictions (strictures) caused by closure of the lumen, such as by scarring or fusion.

In some embodiments, use of device 10 may promote healing in the affected area of the lumen.

Apparatus and methods of the present disclosure can be utilized for anastomosis in various lumens of the body and the intestine in FIGS. 1 and 2 is provided by way of example. Other lumens include for example lumens located in the gastrointestinal tract, the urinary tract, the cardiovascular system, the biliary tract, pancreatic duct and the genitourinary tract. Suitable anastomosis sites may include for example the intestines, esophagus, stomach, bile ducts, pancreas, pancreatic duct, ureter, pancreas and urethra.

Other body lumens/tubular structures and sites are also contemplated. Uses of the device other than for anastomosis are also contemplated.

In one embodiment, resection of a portion of the GI tract such as the esophagus, stomach, colon, small intestine or large intestine may be performed on a patient under general anesthesia to remove troublesome portions of luminal tissue, such as cancerous tissue. After resection, the separated lumen ends may be anastomosed, with device 10 positioned in the luminal tissue.

The device 10 (as well as devices 20 and 30 discussed below) is shown symmetrically shaped but asymmetrical shapes, such as the ends being of different sizes or configurations, are also contemplated as are shapes other than the cylindrical shape shown, e.g., funnel shaped, non-circular cross-section, etc. Additionally, the device may be configured for custom sizing and/or shaping to conform to the contours of the lumen.

The device is preferably non-expandable such that its transverse dimension is the same during insertion as well as during placement. However, in alternate embodiments, the device is collapsible/expandable such that it is inserted in a reduced diameter configuration and expands to a larger diameter placement configuration. Expansion can be for example by an inflatable balloon or by a phase change such as with shape memory polymeric materials.

The device can be configured to be of a size (or expandable to a size in embodiments where the device expands) to make contact with the surrounding luminal tissue, i.e., the internal wall of the lumen, for attachment and/or support. For example, where adhesive is applied to at least part of the external surface of the device and/or at least part of the internal surface of the luminal tissue, a balloon may provide a mechanism for holding the device 10 in place while the adhesive sets.

Device 10 comprises a biocompatible, biodegradable and/or bioabsorbable material. Once in place, it may disintegrate/degrade/resorb over time (once the lumens attach), and either become absorbed into or pass through the body so invasive mechanical removal is not necessary.

The tubular structure preferably provides a continuous outer wall (e.g. without openings) to provide a sealed structure along its length.

In some embodiments, the device can be composed of tissue engineered material. For example, the device can be made of cells of an organ such as colon cells.

Figure 9:
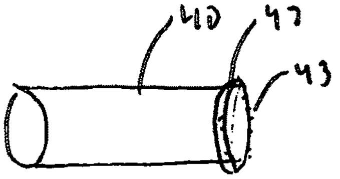
FIG. 9 is a perspective view of an alternate embodiment of the tubular device having a thickened rim portion.

In some embodiments, the device can be formed with a ribbed rim 42 to providing a holding force to hold the device against the tissue/organ, e.g., colon, as shown in FIG. 9. The rim 42 of device 40 can create a radial force against the body lumen, e.g., colon, to help hold it in place. The rim, being at the top, i.e., closer to the head, could also provide a seal to prevent passage of stool behind it. An adhesive can be placed on the tip of the rim of the device to help hold it in place and provide a seal. The top of the device can in some embodiments be thicker to provide additional support as shown for example in FIG. 9. Thus, the device of FIG. 9 serves two functions: securement in place and sealing the body lumen from unwanted passage proximal of the rim 42. In this embodiment, in some instances, the adhesive need only be applied to the rim portion (top), adhesive may be applied to other regions of the device. The adhesive 43 can be applied around the rim periphery (i.e. circumference) as shown in FIG. 9. The adhesive around the rim periphery can provide the sole adhesive or alternatively adhesive could be provided on other regions.

Device 10 can include an adhesive applied thereon during the surgical procedure. The adhesive can be applied to a portion or to the entire external surface during the surgery and then the device inserted into intestinal portions as shown in FIG. 2 wherein the adhesive surface comes in contact with the inner wall of the lumen to adhesively attach the device 10 within the lumen. Note the drawings show the device not in contact with the inner wall of the lumen for clarity, it being understood, that during use the device can be configured to be of a size such that at least portions of the outer wall of the device are in contact (i.e. abutment) with the inner wall of the lumen so the adhesive is pressed between the outer wall 13 of device 10 and the inner wall a3, b3 of the lumens of intestine portions a, b.

Figure 3:
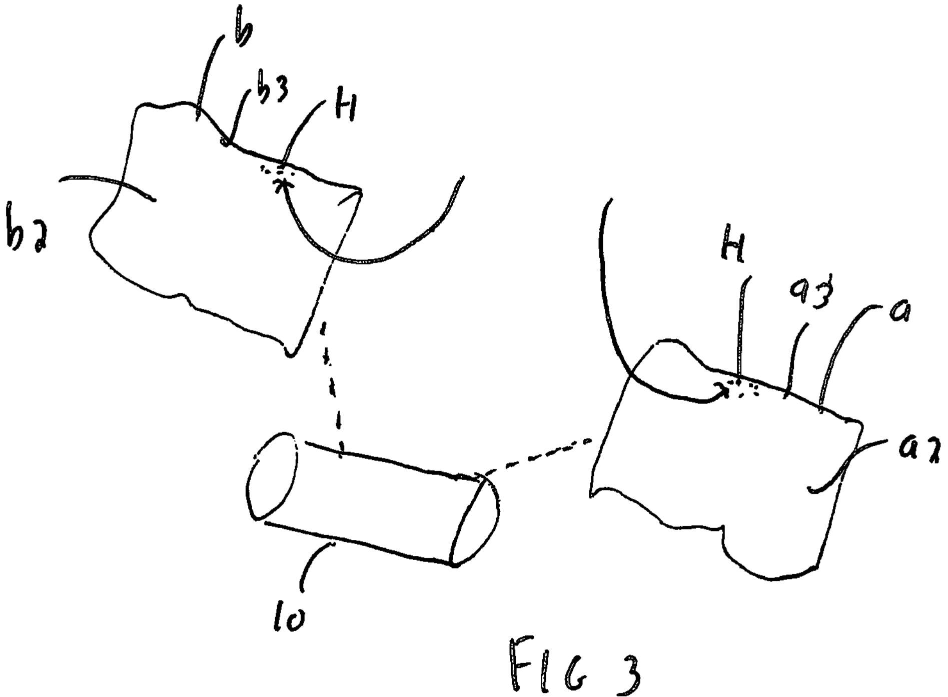
FIG. 3 illustrates an alternate embodiment wherein the adhesive is applied to the internal wall of the lumens of the intestinal portions prior to insertion of the tubular device of FIG. 1.
Figure 4:
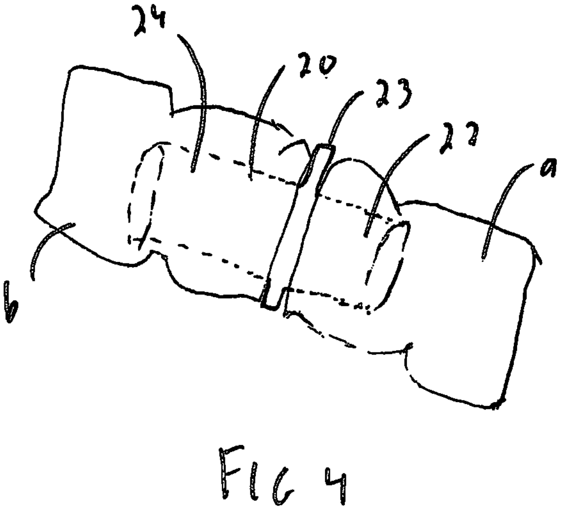
FIG. 4 is a perspective view of an alternate embodiment of the tubular device of the present disclosure having an enlarged region to bridge the gap between the first and second intestinal portions which are not in abutment.

In the alternate embodiment of FIG. 3, the adhesive H is applied solely to the inner wall a3, b3 of intestine portions a, b as shown schematically by the arrows. Device 10, without any adhesive applied thereto, would then be inserted into the lumens a2, b2 after such application of adhesive to adhere to the inner walls a3, b3.

The adhesive, in alternate embodiments, could be applied to device 10 prior to the surgery rather than during the surgery and activated during the procedure. That is, the adhesive could be applied to the external wall of the device 10 prior to the surgical procedure and then activated, e.g., via warming by body temperature, or by another device, to release the adhesive to provide adherence of the device 10 to the lumen walls a3, b3.

In the embodiment of FIG. 2, the device is inserted into the lumens of the two separated intestine portions and the two portions/lumens are brought into contact/abutment for the anastomosis. In the alternate embodiment of FIG. 4, device 20 has an enlarged diameter region 23 between ends 22 and 24 at a midway portion between the two ends or alternatively closer to one of the ends. The enlarged region 23 bridges the gap between intestinal portions a, b, i.e., the portions a, b are in abutment with the enlarged region 23, on opposing sides. In some embodiments, the enlarged region 23 can have an outer diameter substantially equal to the outer diameter of portions a, b, although other outer diameters are also contemplated. In this embodiment, adhesive could also be applied to enlarged region 23 and/or sections a, b where they abut. The ends 22 and 24 are within the lumens of portions a, b and thus have a smaller OD than the ID of portions a, b. Device 20 can be made of the same material, can be of various symmetrical and asymmetrical forms, and function to provide structure in the same manner as device 10.

Figure 5:
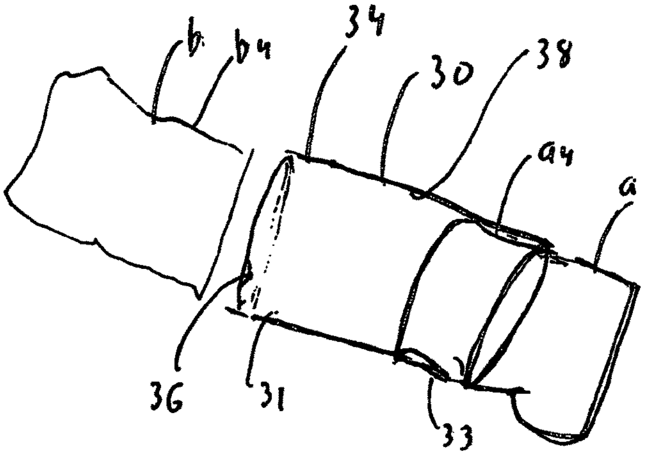
Figure 6:
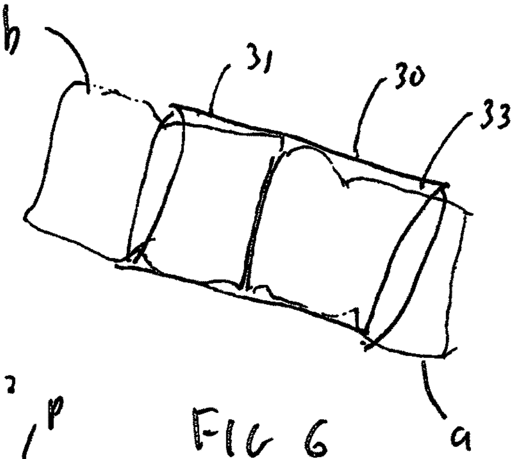
Figure 7:
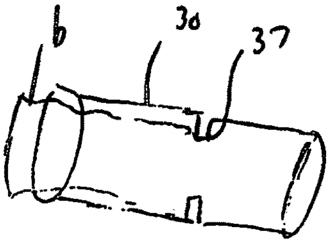
FIG. 7 is a perspective view of an alternate embodiment of the tubular device of the present disclosure having an inward extension.

In the alternate embodiment of FIGS. 5 and 6, device 10 is dimensioned so that it is placed over the external wall of the intestine sections a, b rather than inside the lumen of portions (sections) a, b as in FIG. 1. More specifically, device 30 has a first end 33 and a second opposite end 34 and a wall 38. The device 30 is shown in FIG. 5 placed over the outer wall a4 of intestine portion a. Intestine portion b is then received into lumen 31 of device 30 through opening 36 such that wall 38 is positioned over outer wall b4 of intestine section b. FIG. 6 illustrates the device 30 placed over both intestine sections a, b, and the sections a, b in abutment for anastomosis. As can be appreciated, in this embodiment, the inner diameter of device 30 would be greater than the outer diameter of the intestine portions a, b to accommodate the portions a, b, within its lumen 31. The device 30 could alternatively include an inwardly extending portion for positioning between the two portions a, b such that the portions a, b abut the inward extension rather than each other for anastomosis (see extension 37 of device 30' of FIG. 7).

Adhesive can be applied to the outer wall of the intestine sections a, b for attachment to device 30. Alternatively, an adhesive can be applied to the inner wall of device 30 in lieu of adhesive application to the outer wall of sections a, b or in addition to adhesive application to the outer wall of sections a, b. Device 30 (and device 30') can be made of the same material, can be of various symmetrical and asymmetrical forms, and function to provide structure in the same manner as device 10.

In another embodiment, the devices of the present disclosure can include a composition to promote healing, such as a growth factor, antimicrobial agent, antibody and/or the like. Growth factors comprise cellular proteins that assist in cellular proliferation and differentiation. Antimicrobial agents, including antivirals, antibiotics and antifungals, prevent harmful bacteria, viruses and/or other microbes from infecting the anastomosed site and interfering with the tissue healing and growth processes. Certain types of antibodies may be implemented to bind with foreign objects, such as bacteria and viruses that would be harmful to the healing site if not contained, e.g., preventing strains of bacteria causing leaks. Chemotherapeutic agents can be included on the device to diffuse into the tissue site. Thus, the device in addition to preventing leaks, can serve other healing and/or treatment functions, and its biodegradable aspect avoids having to remove the device after healing or treatment.

Various uses of the devices are contemplated herein. Some examples are provided below, it being understood the devices of the present disclosure can be used in clinical applications and in other parts/regions of the body in addition to those specifically disclosed herein.

In another embodiment, the device could be placed across a stricture (i.e. narrowing) in the lumen of the intestine (or other body lumen) to help keep the lumen open, and the factor applied to the device could be a growth inhibitor. In some embodiments, the growth inhibitor could be low grade chemotherapeutic agent used as an anti-proliferation type drug to inhibit growth, such as paclitaxel.

Figure 8:
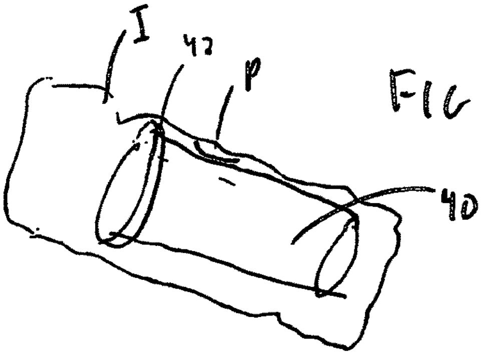
FIG. 8 is a perspective view showing the tubular device inserted into a body lumen to seal a perforation in the lumen.

In another embodiment, the device can be used in perforation of the intestine secondary to diverticulitis or iatrogenic perforation to seal a perforation. Antibiotics can be attached to the device in some embodiments. The device can also be used to seal perforations in other body lumens/parts. FIG. 8 illustrates an example of device 10 used to seal a perforation P in intestine I by way of example. Perforations naturally occur due to a variety of causes such as diverticulitis, ulcers, endoscopic procedures, etc. The biodegradable stent can protect the perforation via a non-invasive or minimally invasive method such that invasive surgery is not required.

Adhesives may comprise any suitable material to attach, adhere and/or bond to living tissue. Adhesives may comprise natural, naturally derived and/or synthetic materials. The adhesive may comprise a gel, liquid and/or solid. Examples of adhesives include purified bovine serum albumin and glutaraldehyde. The adhesive may comprise polyethylene glycol.

In preferred embodiments, the adhesive utilized not only performs an adherence function but also forms a sealing function. This dual function helps to prophylactically prevent leaks. Sealant surgical glue may be used as the adhesive.

Suitable methods of application of the adhesive may include spraying, topical application and/or injection. In one embodiment, a more viscous adhesive may be applied to decrease the setting time, thereby decreasing the time required for a surgeon to hold the ends of lumen together or the ends of a lumen against the device (scaffold). The adhesive may provide both a mechanism for attachment of lumen ends to each other after anastomosis, as well as a sealant to inhibit leakage after reattachment. As described above, the adhesive may bond the device to the lumen ends and may seal the connection between the device and lumen ends to inhibit leakage. In yet another embodiment, the adhesive may be applied over the device and the lumen ends to both bond the lumen ends to the device, as well as provide a seal to inhibit leakage.

In one embodiment, once a biocompatible, biodegradable and/or bioabsorbable adhesive is in place it may be configured to disintegrate, degrade and either become absorbed into or pass through the body. For example, in an application where the lumen ends are configured to heal and reseal themselves, the adhesive may no longer be necessary to bond and/or seal the lumen, and it may be desirable for the adhesive to be removed.

In alternate embodiments, a suture can be used in addition to or in lieu of the adhesive to help secure the device in place. The suture can be for example in the form a "T" that hooks in place. It can be placed in various regions of the device such as at the rim in devices like those of FIG. 9 having a rim.

The device may be used in various methods. In one method to prevent leakage in an intestine, the method includes a) positioning a tubular straw like device across a lumen of the intestine for positioning across an anastomotic site; and b) securing the device to the intestine utilizing an adhesive, the device including a healing or treatment substance adhered thereto. In another method to prevent leakage in an intestine, the method includes a) positioning a tubular straw like device in a lumen of a first intestinal portion to be attached to a second intestinal portion at an anastomotic site, the tubular straw having a rim with an enlarged diameter; and b) securing the device to the intestine utilizing an adhesive, the rim blocking stool passage past the rim. In another method, the device is used to seal a perforation in a body lumen, the method comprising a) positioning a tubular straw like device in the body lumen, the device having a rim having an enlarged diameter to provide a radial force against the intestine; and b) securing the device to a wall of the body lumen utilizing an adhesive, the rim preventing backflow past the rim.

Although the apparatus and methods of the subject invention have been described with respect to preferred embodiments, those skilled in the art will readily appreciate that changes and modifications may be made thereto without departing from the spirit and scope of the present disclosure as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present disclosure.

It will be understood by those skilled in the art that the above particular embodiments are shown and described by way of illustration only. The principles and the features of the present disclosure may be employed in various and numerous embodiments thereof without departing from the scope and spirit of the disclosure. The above-described embodiments do not restrict the scope of the disclosure.

Additionally, persons skilled in the art will understand that the elements and features shown or described in connection with one embodiment may be combined with those of another embodiment without departing from the scope of the present disclosure and will appreciate further features and advantages of the presently disclosed subject matter based on the description provided.

Throughout the present disclosure, terms such as “approximately,” “about,” “generally,” “substantially,” and the like should be understood to allow for variations in any numerical range or concept with which they are associated. It is intended that the use of terms such as “approximately,” “about,” “substantially,” and “generally” should be understood to encompass variations on the order of 25%, or to allow for manufacturing tolerances and/or deviations in design. For example, the term “generally parallel” should be understood as referring to configurations in which the pertinent components are oriented so as to define an angle therebetween that is equal to 180°+25% (e.g., an angle that lies within the range of (approximately) 135° to (approximately) 225°).

The recitation of numerical ranges by endpoints includes all numbers within the range.

Although terms such as “first,” “second,” “third,” etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases “at least one of A, B, and C” and “A and/or B and/or C” should each be interpreted to include only A, only B, only C, or any combination of A, B, and C.

What is claimed is:

1. A method to prevent leakage between at least two lumens of a patient’s body during a resection surgery, the method comprising:

- resecting a portion of a colon of a patient during the resection surgery;
- during the resection surgery:
  - applying an adhesive to each of a first lumen of a first colon portion and a second lumen of a second colon portion;
  - attaching the second colon portion to the first colon portion to form an anastomotic site; and
  - subsequent to applying the adhesive to each of the first lumen and the second lumen, positioning a sealing structure over the first lumen of the first colon portion and the second lumen of the second colon portion, wherein positioning the sealing structure over the first lumen of the first colon portion and the second lumen of the second colon portion forms a seal.

2. The method of claim 1, wherein securing the sealing structure to the first colon portion utilizes a suture such that the sealing structure extends across the anastomotic site, the sealing structure including a treatment or healing substance adhered thereto.

3. The method of claim 2, wherein the sealing structure has a rim, and the suture is placed on the rim provides.

4. The method of claim 2, wherein the suture further provides the seal.

5. The method of claim 2, wherein the healing substance is a growth factor.

6. The method of claim 5, wherein the growth factor comprises cellular proteins that assist in cellular proliferation and differentiation.

7. The method of claim 1, wherein the sealing structure is formed of tissue engineered material.

8. The method of claim 7, wherein the tissue engineered material comprises colon cells.

9. The method of claim 1, wherein the sealing structure is formed of biodegradable materials.

10. A method to seal a perforation in a body lumen, the method comprising:

- resecting a portion of the body lumen during a resection surgery into a first body lumen and a second body lumen;
- during the resection surgery:
- applying an adhesive to each of the first body lumen and the second body lumen;
- attaching the second body lumen to the first body lumen to form an anastomotic site; and
- subsequent to applying the adhesive to each of the first body lumen and the second body lumen, positioning a sealing structure over the first body lumen and the second body lumen, wherein positioning the sealing structure over the first body lumen and the second body lumen forms a seal.

11. The method of claim 10, wherein securing the sealing structure to a wall of the body lumen utilizes a suture, the suture providing the seal.

12. The method of claim 11, wherein the sealing structure has a rim, and the suture is applied only to the rim of the sealing structure.

13. The method of claim 10, further comprising applying a healing or treatment substance to an inner wall of the sealing structure prior to insertion into the body lumen, the substance applied at least at a region adjacent the region adjacent the anastomotic site.

14. The method of claim 10, wherein the sealing structure is formed of tissue engineered materials.

15. The method of claim 10, wherein the sealing structure is formed of biodegradable materials.

16. A method to seal a perforation in a body lumen, the method comprising:

- applying an adhesive to each of a first body lumen and a second body lumen;
- attaching the second body lumen to the first body lumen to form an anastomotic site; and
- subsequent to applying the adhesive to each of the first body lumen and the second body lumen, positioning a sealing structure over the first body lumen and the second body lumen, wherein positioning the sealing structure over the first body lumen and the second body lumen forms a seal.

17. The method of claim 16, wherein securing the sealing structure to a wall of the body lumen utilizes a suture, the suture providing the seal.

18. The method of claim 17, wherein the sealing structure has a rim, and the suture is applied only to the rim of the sealing structure.

19. The method of claim 16, further comprising applying a healing or treatment substance to an inner wall of the sealing structure prior to insertion into the body lumen, the substance applied at least at a region adjacent the region adjacent the anastomotic site.

20. The method of claim 16, wherein the sealing structure is formed of tissue engineered materials or biodegradable materials.

* * * * *